United States Patent
Pauws et al.

(10) Patent No.: US 10,796,560 B2
(45) Date of Patent: Oct. 6, 2020

(54) PERSONAL EMERGENCY RESPONSE SYSTEM WITH PREDICTIVE EMERGENCY DISPATCH RISK ASSESSMENT

(71) Applicant: KONINKLIJKE PHILIPS N.V., Eindhoven (NL)

(72) Inventors: Steffen Clarence Pauws, Eindhoven (NL); Mohammad Hossein Nassabi, Eindhoven (NL); Linda Schertzer, Framingham, MA (US); Tine Smits, Beerse (BE); Jorn Op Den Buijs, Eindhoven (NL); Patrick William Van Deursen, Bussum (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/223,393

(22) Filed: Dec. 18, 2018

(65) Prior Publication Data
US 2019/0122532 A1    Apr. 25, 2019

Related U.S. Application Data

(63) Continuation of application No. 15/317,440, filed as application No. PCT/IB2015/054336 on Jun. 9, 2015, now Pat. No. 10,181,252.
(Continued)

(51) Int. Cl.
*G08B 25/01* (2006.01)
*G16H 10/60* (2018.01)
(Continued)

(52) U.S. Cl.
CPC ......... *G08B 25/016* (2013.01); *G06F 19/00* (2013.01); *G06F 19/3418* (2013.01);
(Continued)

(58) Field of Classification Search
CPC ...... G08B 25/016; G16H 40/67; G16H 10/60; G16H 80/00; G16H 40/40; H04W 4/90; H04L 67/306; G06F 19/00; G06F 19/3418
See application file for complete search history.

(56) References Cited

U.S. PATENT DOCUMENTS

| | | | |
|---|---|---|---|
| 2005/0053209 A1 | 3/2005 | D'Evelyn et al. | |
| 2005/0163302 A1* | 7/2005 | Mock | A61B 5/165 379/211.02 |
| 2006/0224416 A1 | 10/2006 | Lloyd | |
| 2007/0165808 A1* | 7/2007 | Pieraccini | H04M 3/51 379/142.04 |

(Continued)

FOREIGN PATENT DOCUMENTS

| | | |
|---|---|---|
| JP | 2013041479 A | 2/2013 |
| RU | 123649 U1 | 1/2013 |

OTHER PUBLICATIONS

Given et al: "Family Support in Advanced Cancer"; CA Cancer J Clin 2001, vol. 51, pp. 213-231.
(Continued)

*Primary Examiner* — Marcos L Torres

(57) ABSTRACT

In a Personal Emergency Response System (PERS) service, activation of a wearable call device by a PERS client causes a speakerphone console to connect with a PERS call center to enable the PERS client to converse with a call center operator while a PERS client profile is retrieved from a PERS database and displayed on a display component at the PERS call center. From the profile, values of a set of features are generated for the PERS client. An emergency dispatch risk prediction or other risk prediction is computed over a future time horizon for the PERS client based on the generated values of the set of features, and is displayed on the display component. The risk prediction may be wirelessly sent to a mobile device for display on the mobile device.

15 Claims, 7 Drawing Sheets

Related U.S. Application Data

(60) Provisional application No. 62/129,377, filed on Mar. 6, 2015, provisional application No. 62/010,660, filed on Jun. 11, 2014.

(51) Int. Cl.
    *G06F 19/00*     (2018.01)
    *G16H 80/00*     (2018.01)
    *H04W 4/90*     (2018.01)
    *H04L 29/08*     (2006.01)
    *G16H 40/67*     (2018.01)

(52) U.S. Cl.
    CPC ............ *G16H 10/60* (2018.01); *G16H 40/67* (2018.01); *G16H 80/00* (2018.01); *H04L 67/306* (2013.01); *H04W 4/90* (2018.02)

(56) References Cited

U.S. PATENT DOCUMENTS

| | | | |
|---|---|---|---|
| 2010/0295674 A1 | 11/2010 | Hsieh et al. | |
| 2013/0218959 A1* | 8/2013 | Sa | G08B 27/005 |
| | | | 709/204 |
| 2013/0307685 A1 | 11/2013 | Sholder | |
| 2014/0095201 A1* | 4/2014 | Farooq | G16H 50/30 |
| | | | 705/3 |
| 2015/0190577 A1 | 7/2015 | Shaanan et al. | |

OTHER PUBLICATIONS

"Medical Alarm"; Wikipedia Article, Retrieved From the Internet on Sep. 9, 2015 at http://en.wikipedia.org/w/index.php?title=Medical_alarm&oldid=595447623, 4 Page Document.

"Caregiving in the U.S."; National Alliance for Caregiving/AARP, Apr. 2004, 85 Page Document.

\* cited by examiner

PERSONAL EMERGENCY RESPONSE SYSTEM WITH PREDICTIVE EMERGENCY DISPATCH RISK ASSESSMENT

CROSS-REFERENCE TO RELATED APPLICATIONS

This application is a continuation of U.S. patent application Ser. No. 15/317,440 filed on Dec. 9, 2016, which is the U.S. National Phase Application under 35 U.S.C. § 371 of International Application No. PCT/IB2015/054336 filed on Jun. 9, 2015, which claims the benefit of both U.S. Provisional Application Ser. No. 62/129,377 filed Mar. 6, 2015, and U.S. Provisional Application Ser. No. 62/010,660 filed Jun. 11, 2014. These applications are hereby incorporated by reference herein.

FIELD

The following relates generally to the medical arts, and more particularly to the medical monitoring arts, medical emergency response arts, and so forth.

BACKGROUND

Older persons, or persons with certain chronic medical problems or risk factors such as severe obesity, are at a higher risk for certain types of incapacitating medical emergencies such as falling (especially falls resulting in bone fracture or other serious injury), heart attacks, acute asthma attacks or other respiratory emergencies, or so forth. Such persons are at risk for quickly becoming incapacitated and thereby being unable to seek medical assistance. Visiting nurses or in-home caregivers can partially address this problem, but are costly and usually cannot be with the at-risk person at all times. An at-risk person may carry a cellular telephone (cellphone) which can provide rapid access to assistance. However, cellphones are relatively bulky and may not be with the at-risk person during an incapacitating event, or may be lost during the event (e.g. the cellphone may be dropped during a severe fall). Cellphones also usually require significant cognitive capability to operate, and a person in pain after a severe fall, or undergoing a heart attack or asthma attack, may be unable to call for assistance using a cellphone. Another option is for the at-risk person to be admitted to a nursing home or other skilled nursing facility, but this option is also costly and is often contrary to the person's desire to maintain independence.

A Personal Emergency Response Service (PERS) is a dedicated system designed to provide at-risk persons with immediately accessible emergency assistance, so as to enable the at-risk person to continue to enjoy independence. These systems enable at-risk persons to live independently by providing them with peace-of-mind, knowing they have immediate access to emergency assistance if and when needed. In a typical PERS service, the at-risk person is provided with a call button in the form of a necklace-worn pendant or a bracelet. By pressing the call button, speakerphone console in the residence is activated, by which the at-risk person is placed into telephonic contact with an operator at a call center maintained by the PERS organization or provider. Based on the telephone number of the residence, the call center automatically determines the address and identity of the at-risk person, and this information is automatically displayed to the responding call center operator on a computer display, along with a profile of the at-risk person retrieved from a PERS database. This personal profile may include, by way of illustration, name, location, demographic information, a list of the person's known chronic conditions, a list of the person's medications, an identification of the nearest hospital, a list of emergency contacts (spouse, relative, friend), physician information, and so forth. With this information, the call center operator is well-equipped to converse with the at-risk person to assess the person's condition. If appropriate, the operator may call for appropriate assistance, such as notifying a neighbor listed in the person's PERS profile, or calling for an Emergency Dispatch (ED) in order to summon an ambulance to the at-risk person's residence. Additionally or alternatively, the call center operator may talk the person through the medical episode, for example by coaching the person through breathing exercises in order to recover from an asthmatic episode. On the other hand, if the responding call center operator is unable to communicate with the at-risk person who initiated the call, this may suggest the person has already become incapacitated and accordingly the operator immediately calls for an ED.

The following discloses a new and improved systems and methods that address the above referenced issues, and others.

SUMMARY

In one disclosed aspect, a Personal Emergency Response System (PERS) is disclosed. A PERS database stores profiles for PERS clients including at least demographic information and information on past calls to a PERS call center. The information on past calls includes information on past emergency dispatch events initiated by the PERS call center. A PERS server system comprises a PERS server computer programmed to perform operations including: (i) retrieving a profile of a PERS client from the PERS database; (ii) generating values of a set of features for the PERS client from the retrieved profile including at least one emergency dispatch event recency feature; and (iii) computing an emergency dispatch risk prediction for the PERS client over a future time horizon using an emergency dispatch risk model trained on PERS client profiles stored in the PERS database and receiving as input for the computing the values of the set of features generated for the PERS client in operation (ii).

In another disclosed aspect, a Personal Emergency Response System (PERS) is disclosed. A PERS server system includes a PERS server computer and a PERS database storing profiles for PERS clients including at least demographic information and information on past calls to a PERS call center. The information on past calls includes information on past emergency dispatch events initiated by the PERS call center. A PERS call center computer is disposed in the PERS call center and includes a display component. A wearable call device is provided, along with a speakerphone console that is wirelessly activated by the wearable call device to connect with the PERS call center to enable a calling PERS client to converse with an operator at the PERS call center while a profile of the calling PERS client is retrieved from the PERS database by the PERS server computer and displayed on the display component of the PERS call center computer. A mobile device is provided, on which is loaded a mobile device application that programs the mobile device to receive and display information pertaining to at least one emergency dispatch event initiated by the PERS call center for a PERS client.

In another disclosed aspect, a method is disclosed, which is performed in conjunction with a Personal Emergency Response System (PERS) service in which activation of a wearable call device by a PERS client causes a speakerphone console to connect with a PERS call center to enable the PERS client to converse with an operator at the PERS call center while a profile of the PERS client is retrieved from a PERS database and information contained in the profile is displayed on a display component at the PERS call center. The method comprises: (i) from the profile, generating values of a set of features for the PERS client using a computer; (ii) computing a risk prediction for the PERS client over a future time horizon based on the generated values of the set of features for the PERS client using the computer; and (iii) displaying on the display component the computed risk prediction for the PERS client together with the displayed information contained in the profile.

One advantage resides in providing a PERS service with predictive risk assessment, for example to assess the risk over a future time interval of the PERS client requiring an emergency dispatch, or to assess the risk over a future time interval of the PERS client requiring admission to a full-time care facility.

Another advantage resides in providing a call center operator computer of a PERS service in which the computer display provides more efficient and rapid assessment of the state of a calling PERS client.

Another advantage resides in providing "informal caregivers" such as relatives, friends, neighbors, visiting nurses, or the like, with information on the PERS profile of a PERS client via a mobile device. Optionally, the predictive risk assessment is also provided via the mobile device.

Another advantage resides in providing information regarding the PERS clientele at highest risk for emergency dispatch (or some other risk).

Another advantage resides in providing an estimate of the number of emergency dispatch events to expect over a future time interval.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
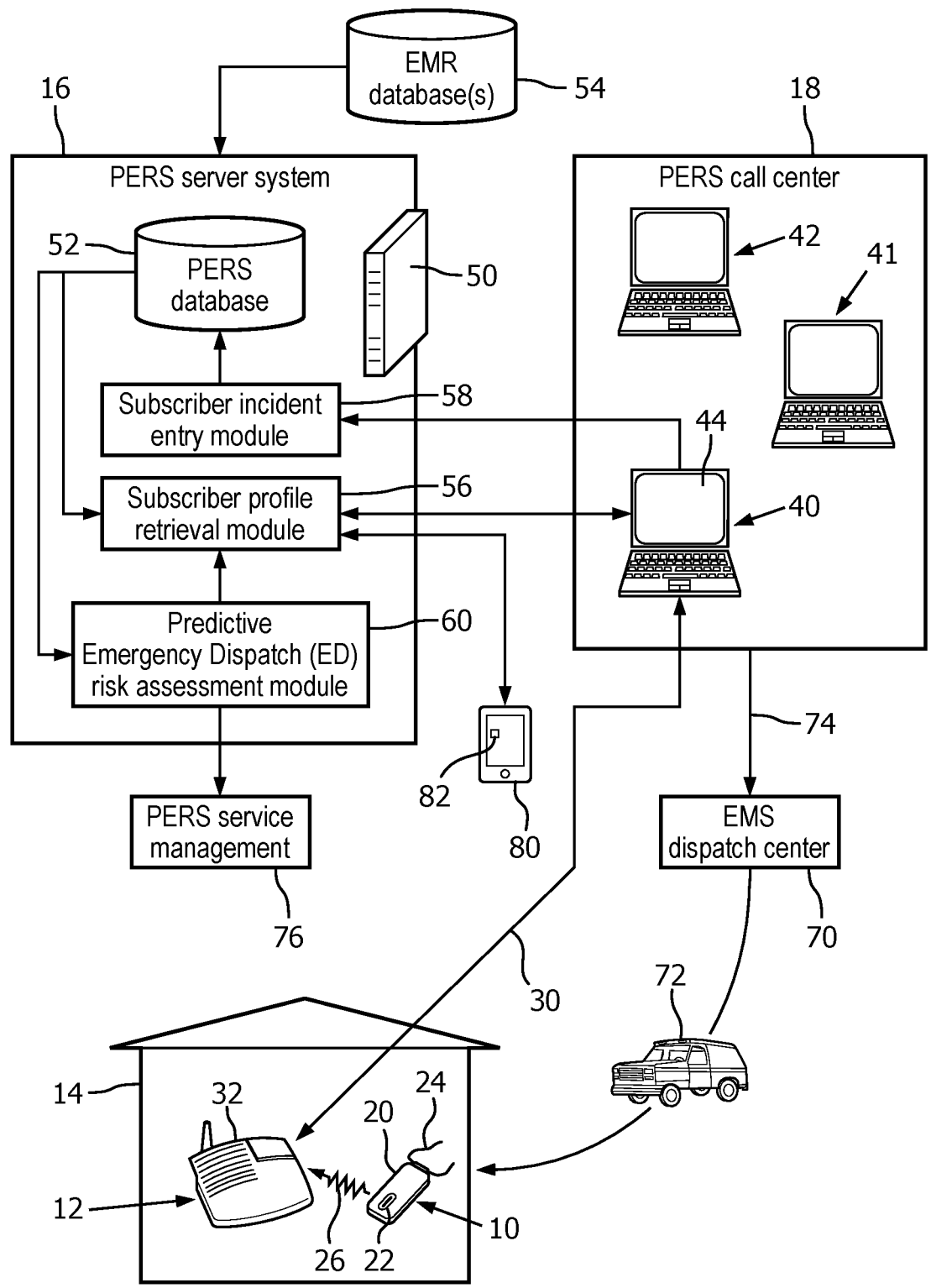
FIG. 1 diagrammatically illustrates a Personal Emergency Response System (PERS) including a predictive Emergency Dispatch (ED) assessment module as disclosed herein.

Disclosed herein are Personal Emergency Response System (PERS) services (and/or supporting equipment and/or infrastructure) that provide predictive estimates of the likelihood (over some time horizon) that an at-risk person served by the PERS service will require an Emergency Dispatch (ED). This ED risk prediction provides a quantitative ED risk assessment for a person served by the PERS service, which may be variously used. For example, the ED risk prediction for a caller to the call center may be computed and displayed on the display viewed by the call center operator while handling the call. This information assists the call center operator in making the important decision of whether to call for an ED, and can be used for other purposes such as prioritizing incoming calls. In another application, the ED risk predictions are computed for all subscribers to the PERS service and the results are analyzed statistically to estimate the number of ED events likely to occur over the time horizon, and/or the results are ranked by risk value to identify subscribers at highest risk of needing an ED so that proactive intervention may be considered for those high-risk subscribers. In some embodiments, the ED risk assessment is performed for different types of emergencies, e.g. a quantitative ED risk prediction may be computed for each of: an ED in response to a fall; an ED in response to a heart attack; an ED in response to respiratory distress; or so forth. This more detailed ED prediction information may be used, for example, to alert EMS personnel to the most likely type of emergency in the event that the caller is unable to communicate this information to the call center operator.

The term "Emergency Dispatch" or "ED" as used herein denotes a response to a medical emergency in which an ambulance or other Emergency Medical Service (EMS) vehicle is dispatched to the residence of a person needing emergency assistance, where EMS personnel traveling in the EMS vehicle assess the medical condition of the person undergoing the medical emergency. An ED event may further include using the dispatched EMS vehicle to deliver the person to a local hospital if medically appropriate. In illustrative embodiments herein, an ED event is counted if an ambulance or other emergency vehicle is dispatched to the residence, regardless of whether or not the person is actually taken to the hospital.

In alternative embodiments, an ED event may only be counted if the person is actually taken to the hospital (that is, in such alternative embodiments, an ED event is not counted if an ambulance is dispatched but EMS personnel arriving via the ambulance determine that the person does not need to be taken to the hospital). In yet other alternative embodiments, counts are maintained of both instances: a count of ED events in which an emergency vehicle is dispatched to the residence, and a (lower) count of the sub-set of those ED events in which the person is actually delivered to the hospital.

The ED service may be provided by the local government (e.g. city, county, et cetera), or by a private entity such as a private ambulance service contracted by a city to provide EMS service. In a typical sequence, an ED event is initiated by dialing a designated emergency telephone number, such as by dialing "911" in North America, or by dialing "112" in Europe. In the case of an ED initiated by a PERS call center, the call center operator may use the conventional "911" or "112", or may use a different communication link to the EMS service. The call center operator may need to instruct EMS personnel as to the identity and address of the at-risk person needing emergency assistance, and/or may provide further information such as the nature of the emergency, known chronic conditions, or so forth.

For convenience, the at-risk person served by the PERS service is referred to in the illustrative examples herein as a "PERS subscriber" or simply as a "subscriber". This reflects a common implementation as a PERS subscription service in which the subscriber (or a friend or relative of the subscriber) pays a recurring (e.g. monthly) subscription fee to maintain ongoing access to the PERS service. The subscription fee may also bundle recurring rental fees for equipment such as a speakerphone console and a wearable call device. While this nomenclature is used for convenience, it is to be understood that a "subscriber" may have other arrangements or relationship with the PERS service—for example, the subscriber may be provided with PERS service without cost to the subscriber, for example if the PERS service is provided for free to at-risk residents as a component of the local EMS service; or the PERS service may be provided by a medical insurance company or other private entity, or by the military in the case of at-risk military personnel or military veterans; or so forth. A more general term is "PERS client" or simply "client" which encompasses illustrative PERS subscribers, and additionally encompasses at-risk persons served by the PERS service under other arrangements such as being sponsored by the local government, by an insurance company, employer, or other private entity, by a military veterans' organization, or so forth.

With reference to FIG. 1, an illustrative PERS service infrastructure includes the following components: a wearable call device 10 for each PERS subscriber; a communicator or speakerphone console 12 for each residence 14 of a subscriber; a PERS server system 16, and a call center 18. Illustrative FIG. 1 shows a single residence 14 with a single communicator 12 and a single wearable call device 10 suitably worn by a subscriber (not shown) for illustrative purposes. It will however be understood that the PERS system serves a population of subscribers living in residences distributed over the geographical area serviced by the PERS, with each subscriber having his or her own wearable call device 10 and associated communicator 12. If the residence 14 is sufficiently large, there may be two or more communicator units in the residence to provide full coverage of all areas accessed by the subscriber. The illustrative wearable call device 10 is a pendant 20 with a large, easily pressed call button 22 that is worn around the neck via a necklace 24 (shown in part). More generally, the wearable call device can have any suitable wearable form factor, such as the illustrative necklace-worn pendant, or a bracelet, or so forth, and includes simple and effective mechanism such as the illustrative push button 22 for triggering a call to the PERS call center 18. The call device 10 is suitably battery-powered to enable complete portability. While the illustrative (preferably large) push button is a convenient call trigger mechanism, other call trigger mechanisms are contemplated, such as a voice-activated trigger mechanism. It is also contemplated to provide a wearable call device that automatically triggers a call based on certain input. For example, the wearable call device 10 may include an accelerometer, and the call device 10 triggers a call upon the accelerometer detecting a rapid downward acceleration (i.e. a sudden falling) of the subscriber wearing the call device 10. The wearable call device 10 optionally has other attributes such as optionally being waterproof so it can be worn in a bath or shower. Pushing the call button 22 or otherwise activating the call device 10 causes the call device 10 emit a wireless signal 26 (e.g. a short-range radio frequency signal) that is received by the communicator 12 to initiate a call to the PERS call center 18. The wearable call device 10 may optionally have other buttons or user inputs, such as an LED indicator light or LCD display providing information such as battery power level; however, the call device 10 is preferably designed to be very simple to operate (e.g. just the illustrated call button 22 in some embodiments) so that the subscriber can operate it even when in significant medical distress or even when under (e.g. medically related or pain-induced) cognitive deficiency.

The communicator or speakerphone console 12 in the residence 14 provides intercom functionality. When triggered by the call device 10, the communicator 12 automatically establishes a communication link 30 with the PERS call center 18 via which the subscriber can communicate with a call center operator. In some PERS service configurations, the communication link 30 is a telephonic link via a telephone landline. This approach has the advantage that the PERS call center 18 can automatically identify the subscriber based on the telephone number associated with the communicator 12. In other embodiments, the communication link 30 is a wireless link, for example via a 3G or 4G wireless cellphone network. Various combinations are also contemplated, such as having a plurality of communicators distributed throughout the residence each wirelessly connected with a main base station via WiFi or another wireless communication protocol, with the main base station then telephonically linked with the call center via telephone landline. The communicator 12 includes a loudspeaker 32 that has sufficient power to be heard by the subscriber throughout the residential area covered by the communicator 12, and likewise has a microphone (not shown) that picks up the subscriber's voice. As already mentioned, more than one communicator may be located in the residence 14 if needed to provide full area coverage. In some embodiments, the microphone is located in the wearable call device 10 and the microphone signal is wirelessly transmitted from the call device to the communicator 12 via suitable modulation of the wireless signal 26.

At the PERS call center 18, the communication link 30 is established with an illustrative computer 40 used by a call center operator (not shown). For illustrative purposes, further operator computers 41, 42 are also shown to diagrammatically illustrate that the call center 18 typically has a number of operators, each with an associated computer 40, 41, 42, sufficient to ensure that there is always a call center operator to handle a subscriber's call. The requisite number of call center operators, and hence the requisite number of computers 40, 41, 42, depends upon the number of PERS subscribers assigned to the call center 18 and the statistical frequency and duration of subscriber calls. The PERS call center 18 has a call routing system (not shown) that routes each incoming subscriber call to the computer of an available call center operator. The computer 40 includes a display component or device 44, a microphone (not shown) to pick up the call operator's voice and a loudspeaker (not shown)

via which the subscriber's voice is heard, so as to enable a two-way audio conversation to be conducted between the calling subscriber and the call center operator handling the call. Upon receipt of the call, a caller ID unit or module (not shown) identifies the telephone number of the calling communicator unit 12. If the communication link 30 is not a telephonic link, then another automated identification system is preferably employed that is suitable for the type of communication link being used. The automatically detected identifier (e.g. the telephone number acquired by the caller ID) is sent to the PERS server system 16.

The PERS server system 16 is suitably embodied by a server computer 50 and a PERS database 52, the latter of which may be implemented as a RAID disk array, multiply redundant hard disk drive system, or so forth. The computing and data storage hardware 50, 52 may be variously implemented and variously located, such as in the form of a server computer located on-site with the PERS call center 18, or located remotely from the PERS call center 18, or implemented as a distributed or cloud computing architecture with the server computer 50 implemented as a networked or otherwise operatively interconnected plurality of computers. The server computer 50 is programmed to perform PERS data storage, retrieval, and processing functionality as described herein. This functionality includes initial subscriber setup (not indicated in FIG. 1) including setting up the initial subscriber profile information (e.g. name, address, telephone number, contacts information, physician information, demographic information such as age, sex, et cetera, known chronic conditions at the time of initial subscription, and so forth). The setup information may be obtained from various sources, such as subscription forms filled out by the subscriber (or by a friend or relative of the subscriber with authorized access to the subscriber's information, or using online forms filled out by a subscription consultant employee of the PERS system in consultation with the subscriber). Some setup information is optionally obtained automatically from available database(s)—for example, patient medical information is optionally automatically acquired by the PERS server system 16 from one or more Electronic Medical Record (EMR) databases 54. Further such functionality is diagrammatically indicated in FIG. 1 as a subscriber profile retrieval module 56, a subscriber incident entry module 58, and a predictive emergency dispatch (ED) risk assessment module 60. In responding to the illustrative call, the telephone number of the communication link 30 determined by caller ID is sent to the subscriber profile retrieval module 56, which accesses the PERS database 52 to retrieve the subscriber profile corresponding to that telephone number and send the retrieved subscriber profile to the computer 40 where pertinent subscriber information is displayed on the display device or component 44 for viewing by the call center operator. This information may include, for example: subscriber name (including any "nickname"); demographic information (gender, age, ethnicity); residence address; residence type (single floor, multi-floor, etc); past incidents history; time since last ED (if any); number of ED events in past two years; etc. The subscriber information is also communicated to the predictive ED risk assessment module 60 which generates an ED risk prediction for the calling subscriber, and this ED risk prediction is also sent to the computer 40 for display on the display device or component 44. The call center operator thus has access to this information, including the ED risk prediction of the caller, so as to be well-equipped to converse with the calling subscriber to assess the subscriber's medical condition and make a decision as to the appropriate call resolution.

If the call center operator determines that ED is the appropriate action, then the operator contacts the local Emergency Medical Service (EMS) dispatch center 70, which dispatches an ambulance or other EMS vehicle 72 to the residence 14. The communication link 74 via which the call center operator contacts the EMS dispatch center 70 may be an emergency telephone number (e.g. "911" in North America, or "112" in Europe), or may be a dedicated wired and/or wireless communication link to the EMS dispatch center 70 such as a dedicated single-purpose landline. In typical PERS response protocols, if the call center operator is unable to effectively communicate with the calling subscriber via the link 30, then an ED will be the initiated. If effective communication is possible, then the decision of whether or not to initiate ED will depend upon the medical assessment made by the operator based on the communication.

Regardless of the type of call resolution, the call center operator enters a subscriber incident report for the call via the computer 40, which is stored via the subscriber incident entry module 58 in the PERS database 52, and more particularly in the subscriber's profile or record in the PERS database 52. For auditing purposes, such an incident report is typically filed by the operator even if the call turns out to be an accidental call (that is, a call inadvertently made by the subscriber by accidentally pressing the call button 20 on his or her call device 10, or a check-in call (that is, a call intentionally made by the subscriber for the purpose of verifying operation of the PERS communication link 30, or for the purpose of engaging the call center operator in conversation, or for some other purpose that is not related to a medical emergency), or a call that does not require an ED or other significant remedial action. Typically, the incident report includes information such as date/time of call, duration, operator identification (these information are typically automatically recorded), call type (check-in, accidental, medically related), and call resolution information (such as information on the ED call if one was made, or a statement that a particular neighbor was contacted if that was the action taken, or so forth). The incident information is added to the subscriber profile.

As described above, the ED risk prediction generated by the predictive ED risk assessment module 60 is advantageously provided to the call center operator via the computer 40 for consideration in handling a subscriber call. Additionally or alternatively, the ED risk prediction may be used for other purposes. In illustrative FIG. 1, the predictive ED risk assessment module 60 may run a risk report of the risk of ED for all subscribers serviced by the PERS for use by PERS service management 76. The ED risk report may, for example, provide anonymized ED risk prediction information in the form of an ED risk distribution histogram or curve, and/or may include a list of those subscribers whose ED risk prediction is higher than a chosen threshold, so that proactive action may be taken for those subscribers at high risk of needing emergency dispatch.

In another application of the ED risk prediction, the subscriber profile along with the ED risk prediction may be provided to a relative, caregiver, or friend via a mobile device 80 on which is loaded a mobile device application ("app") 82 (diagrammatically indicated in FIG. 1 by an icon indicating the app 82. The mobile device 80 may, for example, be a cellular telephone, a tablet or slate computer, or the like. In the case of a mobile device app 82 providing subscriber information to third parties, some information of the subscriber profile may optionally be omitted in compliance with applicable privacy regulations, e.g. HIPAA in the United States. (Likewise, it is to be understood that the PERS service as a whole is expected to comply with all HIPAA or other applicable medical data privacy regulations, for example by obtaining informed written consent from the subscriber before acquiring and storing medically related subscriber information).

Figure 2:
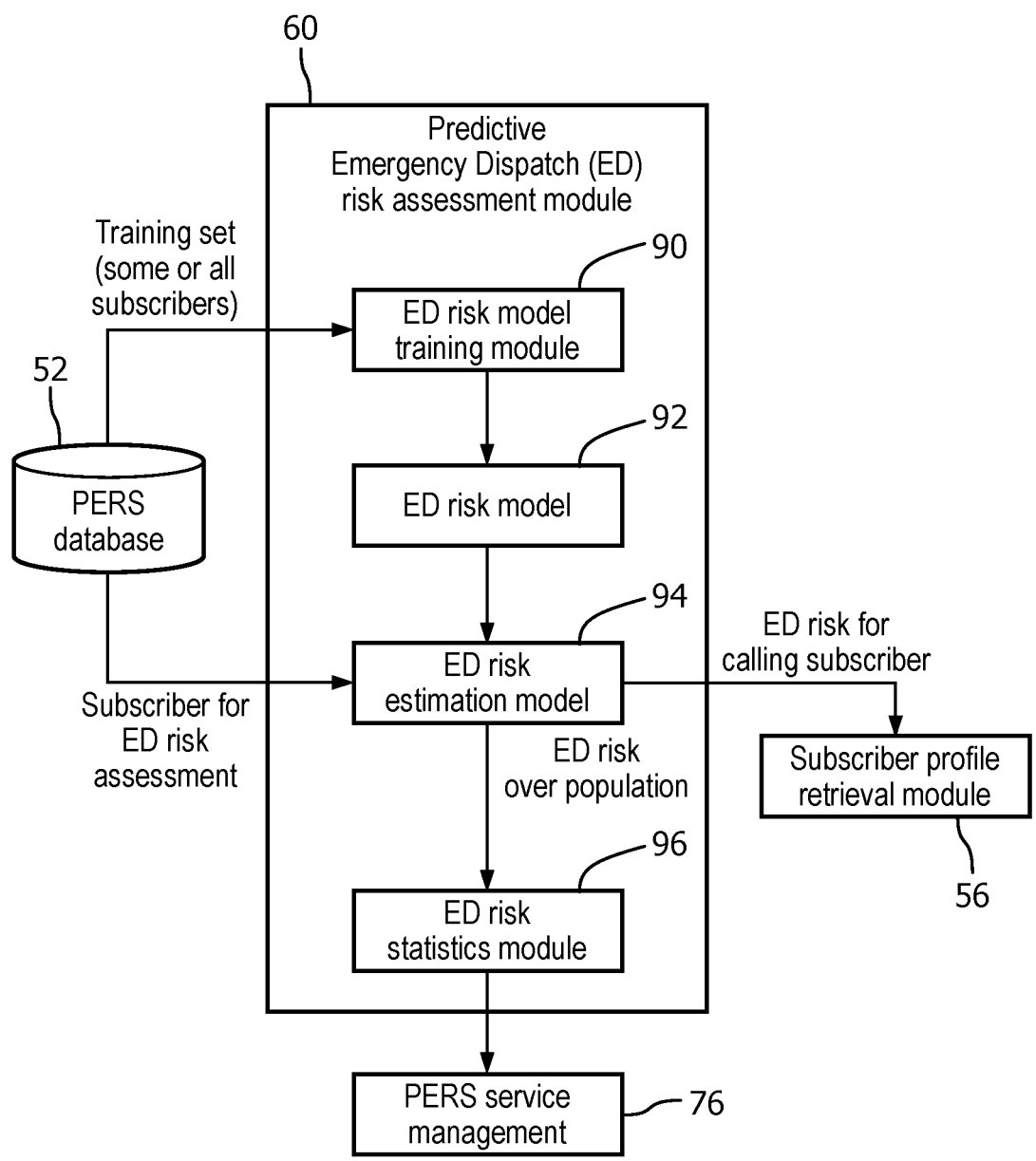
FIG. 2 diagrammatically illustrates a suitable embodiment of the predictive ED assessment module of FIG. 1.

With reference to FIG. 2, an illustrative implementation of the predictive ED risk assessment module 60 is described. An ED risk model training module 90 trains an ED risk model 92 using training data comprising subscriber profiles extracted from the PERS database 52. In some illustrative embodiments herein, a multivariate logistic regression model is employed to train the ED risk model 92; however, substantially any other type of model can be employed, such as multivariate linear regression model, a Naïve Bayesian model, a neural network, or so forth. The trained ED risk model 92 is used by an ED risk estimation module 94 to provide an ED risk prediction for a subscriber based on the subscriber's current profile retrieved from the PERS database 52. An ED risk statistics module 96 is optionally provided to perform statistical or other analysis on the ED risk predictions of the subscribers in the PERS database for use by PERS management or providers of a PERS service 76.

Figure 3:
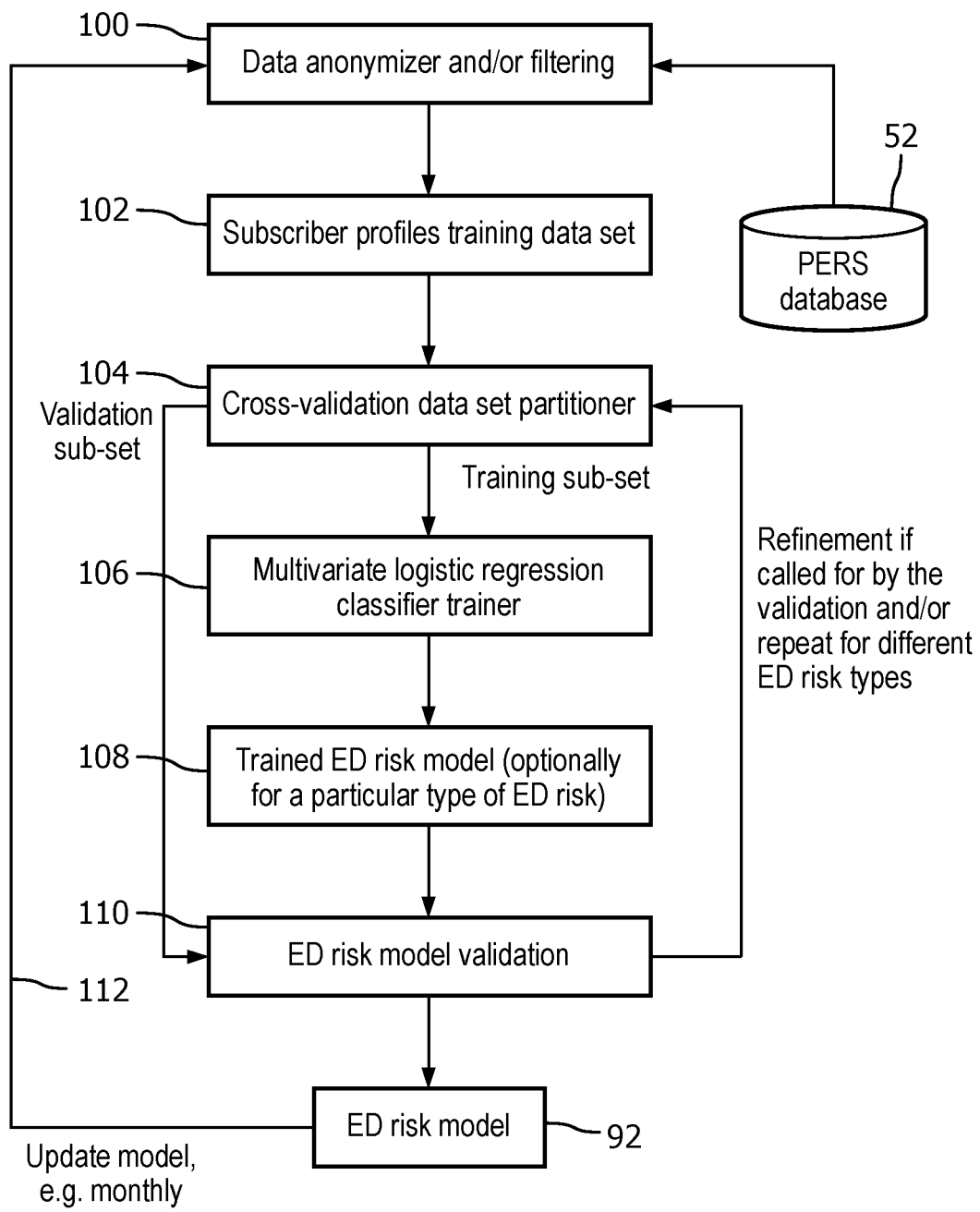
FIG. 3 diagrammatically illustrates an ED risk model training process suitably performed by the predictive ED assessment module of FIGS. 1 and 2.

With reference to FIG. 3, an illustrative training method suitably performed by the ED risk model training module 90 is described. In an operation 100, a subscriber profiles training data set 102 is extracted from the PERS database 52. The operation 100 may optionally include data anonymization, filtering (e.g. to remove subscriber profiles that are too short, e.g. a subscriber who only subscribed to the PERS service a month ago may not have enough history to be useful for training), or so forth. The subscriber profiles can be used as annotated training data as follows (where the prediction time horizon is assumed to be thirty days): for each subscriber, if an ED was made for that subscriber in the last 30 days then the subscriber is labeled as a positive sample; if no ED was made for that subscriber in the last 30 days then the subscriber is labeled as a negative sample. For each subscriber, a feature set is generated. Some illustrative features may include some or all of the following: subscriber demographic information (age, gender, ethnicity, et cetera); self-reported medical conditions; medical conditions obtained from the Electronic Medical Record (EMR) database 54 (if available); the time interval since the last ED for the subscriber; the last hospitalization of the subscriber; the number of ED calls for the subscriber over a past time horizon (e.g. 2 years in some illustrative examples); the number of days of hospitalization in this past time horizon; the type of residence (a subscriber may be more likely to have a serious fall in a multi-floor residence as compared with a single-floor residence); and so forth. Features such as the time interval since the last ED, or the time interval since the last hospitalization, quantify time since the last such event, and are referred to herein as "recency" features. Features such as the number of ED calls or the number of hospitalization days, quantify the number or frequency of such events (typically over some past time horizon, e.g. over the last two years), and are referred to herein as "frequency" features. It is contemplated to adjust features in various ways, such as by discounting older ED calls in computing the value of an ED frequency feature.

In addition to the foregoing features, experiments have indicated some additional features that exhibit surprising correlation with the ED risk, and hence which are suitably used as features in the training data set 102. One such feature relates to the number of check-in calls made by the subscriber. A check-in call is a call intentionally made by the subscriber for the purpose of verifying operation of the PERS communication link 30, or for the purpose of engaging the call center operator in conversation, or for some other purpose that is not related to a medical emergency. A higher frequency of check-in calls by the subscriber has been found to positively correlate with subsequent ED events for the subscriber. Without being limited to any particular theory of operation, it is believed that a high frequency of check-in calls may be indicative of a high level of anxiety on the part of the subscriber. In some cases, this anxiety may be physiologically based, for example due to breathing difficulty, incipient cardiac problems, or the like, which may not (yet) be consciously recognized by the subscriber.

In a specific implementation, the subscriber is asked to check-in when he or she receives a specific signal, or at predefined regular check-in time points. During a check-in, voice communication with the call-center is established or a specific action is performed by the subscriber to give an indication that everything is ok. Features for the ED risk assessment can represent adherence of the subscriber to these 'check-in rules'. It is anticipated that subscribers which are ok will adhere to these rules or will even skip a check-in, while subscribers with anxiety might check-in more than required to be sure help is within reach if needed.

Another feature found to correlate with ED risk, and hence suitably used as a feature in the training data set, is accidental calls that are inadvertently made by the subscriber by accidentally pressing the call button 20 on his or her call device 10. Again without being limited to any particular theory of operation, it is believed that a high frequency of accidental calls may be indicative of increasing forgetfulness or mental debility on the part of the subscriber. Such a condition may lead to increased likelihood of accidents (e.g. serious falls), leading to ED events, or may have a physiological basis (e.g. reduced blood flow due to a cardiac problem, or reduced blood oxygenation due to a respiratory problem) that may be leading to an ED event.

If the wearable call device 10 includes an accelerometer or other "automatic fall detector", this can optionally be used to generate additional features. For example, false alarms from the automatic fall detector can be used as a feature representing 'near falls' or potentially dangerous situations.

With continuing reference to FIG. 3, the illustrative training module employs a cross-validation data set partitioning operation 104 that partitions the training data into a training sub-set and a validation sub-set. In a training operation 106, the training sub-set is used to train a multivariate logistic regression model with time-dependent covariates (or, in other embodiments, a training operation employing a linear or logistic regression model, decision trees, adaptive boosting, random forests, or other type of model training algorithm) to generate a trained ED risk model 108. In illustrative examples herein, a multivariate logistic regression model was used for calculating the likelihood of an impending ED. The logistic regression model describes how the different factors increase or decrease the risk (for ED transport, in this case). The log regression formula for a subscriber denoted by index i may be written as:

$$p_i(x) = \frac{1}{1 + e^{-(\beta_0 + \beta_1 x_{i1} + \beta_2 x_{i2} + \ldots + \beta_k x_{ik})}}$$

where $p_i(x)$ for subscriber i is the probability of having an ED in the next 30 days and is calculated considering the coefficients β in the regression formula. The terms $x_{i1}, \ldots, x_{ik}$ denote the values for subscriber i of the k features of the feature set, and the coefficients $\beta_1, \ldots, \beta_k$ are coefficients for the k features of the feature set that are optimized by the training operation 106 to produce the ED risk-predictive model. Again, this is merely one illustrative ED risk model, and other model designs may be employed, such as a linear regression model, a decision tree, an adaptive boosting model, a random forests model, or so forth.

In general, the model is designed to (1) receive as inputs values for the set of features obtained from a subscriber profile, and (2) output an ED risk prediction which is a value indicative of the risk of the subscriber requiring an ED in the event horizon time (e.g. in the next 30 days in the illustrative examples). The ED risk prediction may be variously presented. In some embodiments, the ED risk model is designed to output a probability, that is, a risk prediction in the range [0,1] which can then be presented as a percentage value (e.g., with a low percentage value indicating a low likelihood of ED being required, and a percentage value near 100% indicating a very high likelihood of ED being required in the next 30 days). In other embodiments, the ED risk is quantized, so that the output is, for example, one of the following quantized values: "low risk", "moderate risk", "high risk". The goal of the training operation 106 is to choose values for parameters of the ED risk model so as to maximize agreement between the ED risk predicted by the model and the actual ED annotations of the training data, while avoiding overfitting and generating generalizable predictions.

In an ED risk model validation operation 110, the validation data sub-set is used to perform validation of the model 108. This validation entails inputting the validation subscriber samples (or more particularly, their respective feature sets) into the ED risk model 108 and assessing the number of false positives, and/or the number of false negatives, or otherwise assessing the performance of the ED risk model 108. If validation is successful (e.g. the number of false positives and/or false negatives is/are sufficiently low) then the ED risk model 108 becomes the ED risk model 92 of the predictive ED risk assessment module 60. If the validation is unsuccessful (e.g. too high a false positive rate, and/or too high a false negative rate) then process flow returns to block 100 (or, alternatively, to block 104) to perform further refinement of the ED risk model.

In the just-described training process, it is assumed that the ED risk model 92 is for the overall ED risk. In some embodiments it is additionally or alternatively desired to train ED risk models for various types of ED risk, such as for the risk of an ED for a serious fall, for the risk of an ED for an acute cardiac condition, for the risk of an ED for respiratory difficulty, or so forth. Here, the subscriber profiles are suitably annotated as follows (where the prediction time horizon is again assumed to be thirty days): for each subscriber and for each risk type, if an ED for that risk type was made for that subscriber in the last 30 days then the subscriber is labeled as a positive sample for ED in response to that type of risk; if no ED for that risk type was made for that subscriber in the last 30 days then the subscriber is labeled as a negative sample for ED in response to that type of risk. The training operations 104, 106, 108, 110 are then independently performed for each risk type (using the positive/negative sample annotations for that risk type) in order to generate an ED risk model for each risk type. In this case, the final ED risk model 92 actually comprises a plurality of ED risk models, one for each risk type and possibly also one for undifferentiated ED risk. (In an alternative approach, known techniques for training a single multi-label output model may be employed, which advantageously may enable leveraging of correlations between the different risk types).

The ED risk factors are not expected to change rapidly over time. However, some change is possible. For example, PERS service operational guidelines may be updated occasionally, and such an update may result in a change to the criteria for initiating an ED. Similarly, EMS protocols may be updated periodically, and such an update may result in different criteria being applied to decide when to transport a person to the hospital. ED risk factors may also be impacted by technology developments (e.g., new monitoring devices), demographic changes (e.g. an aging population), improved medication options, and so forth. To account for such changes over time, an ED risk model update may be initiated 112 on some basis, e.g. monthly, or every two weeks, etc. Advantageously, parameters of the existing ED risk model 92 may be used as initial values for the model update, and since the ED risk factors are expected to change relatively slowly over time, the model update is generally a fast process.

Figure 4:
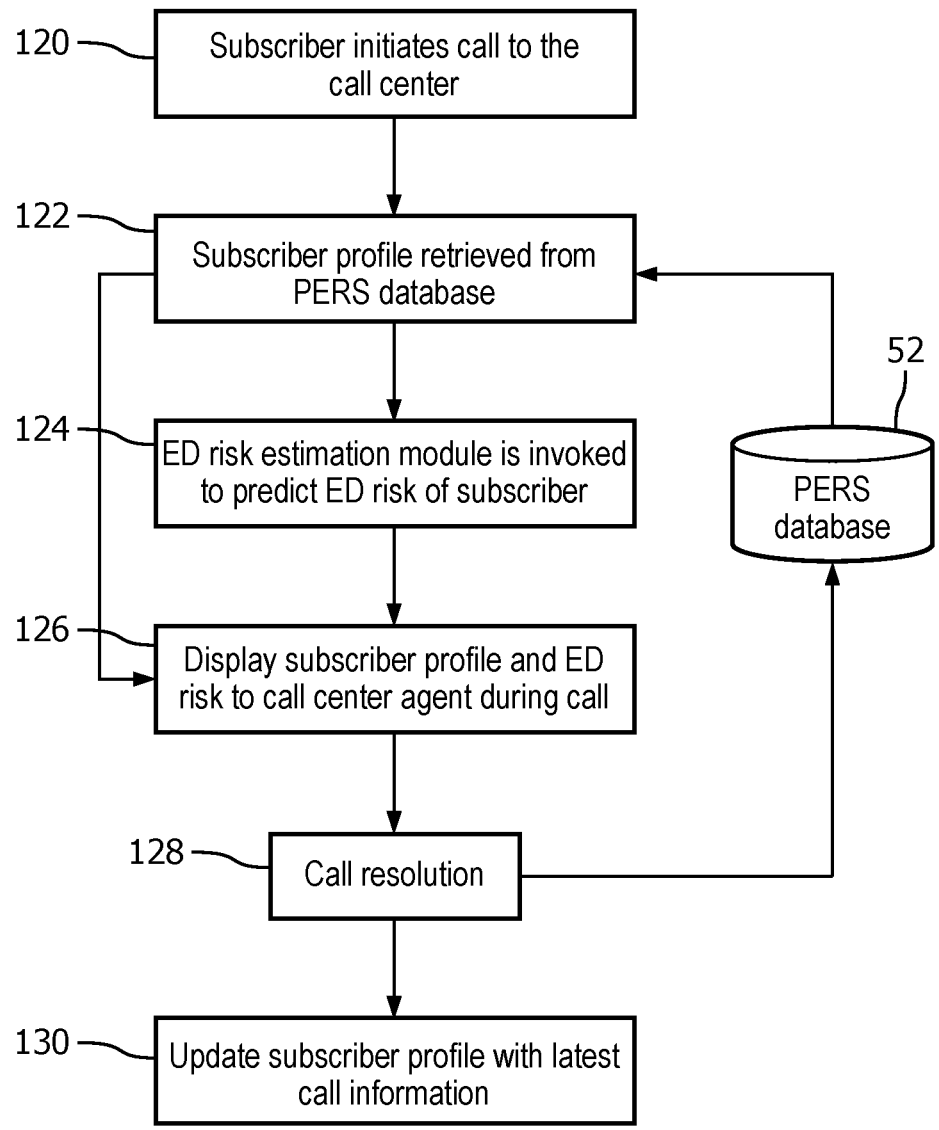
FIG. 4 diagrammatically illustrates processing of a subscriber call to the PERS call center of FIG. 1 including operation of the predictive ED assessment module of FIGS. 1 and 2 in conjunction with handling the subscriber call.

With reference to FIG. 4, an illustrative method suitably performed by the ED risk estimation module 94 in the context of a subscriber call is described. In an operation 120, a subscriber initiates a call to the PERS call center 18 by activating his or her wearable call device 10. A caller ID component or other automatic caller identification subsystem of the PERS call center 18 identifies the calling subscriber, and in an operation 122 the subscriber profile is retrieved from the PERS database 52. In an operation 124, the ED risk estimation module 94 is invoked to predict the ED risk for the calling subscriber. To this end, values for the same set of features as was used in the training process (FIG. 3) are extracted from the calling subscriber profile retrieved in the operation 122. The features set extracted from the profile retrieved in the operation 122 includes any "new" profile data that was generated since the ED risk model 92 was trained—for example, the time-since-last-ED recency feature reflects any ED events that have occurred since the model training. (The feature set for the subscriber does not, however, reflect any updates that will be incurred due to the current call). Depending on how the ED risk model 92 is designed, the model output may be an ED risk probability running between 0 (virtually no risk of an ED in the next 30 days) and 1 (very high risk of an ED in the next 30 days). If the ED risk model 92 includes models for different risk types (falling, cardiac, respiratory, etc) then the operation 124 suitably applies each such type-specific ED risk model to generate ED risk predictions for each of the different risk types.

In an operation 126, the subscriber's profile is displayed on the display device 44 of the computer 40 used by the call center operator handling the call (see FIG. 1), along with display of the ED risk prediction (or risk predictions, in the case of predictions for different risk types). If the ED risk is high, it may optionally be displayed in a highlighted format, e.g. using red font color, flashing, or so forth. In one contemplated embodiment, the ED risk prediction displayed in the form of a gauge. In another contemplated, embodiment the ED risk prediction displayed in the form of a traffic light with red=high risk, yellow=medium risk, green=low risk. Optionally, a high-risk subscriber may be flagged with a red flag indicator or other indicator. Optionally, the risk history of the subscriber can be computed as a function of time (e.g. by artificially removing data generated after a certain time to compute the ED risk at that certain time, and repeating for several different times prior to the present) and the results can be shown as a line or bar chart to indicate whether the subscriber's ED risk has increased over time.

The displayed ED risk prediction enables the call center operator to take into account the ED risk in assisting the caller. For example, the operator may spend more time with high risk subscribers and elicit more information from them related to underlying risk factors. The call center operator converses with the subscriber (if possible), and develops a call resolution 128, which may include an ED initiation if appropriate, or may constitute calling a neighbor, or talking the subscriber through a medical episode if appropriate. If the call is a check-in call, the call resolution 128 is to log the call as a check-in call. If the call is an accidental call, the call resolution 128 is to log the call as an accidental call, possibly in conjunction with noting any noteworthy aspects of the call (such as the cognitive state of the subscriber). In an operation 130, the call center operator updates the subscriber profile with the latest call, including the date/time stamp (typically automatically recorded), recording any self-reported medical condition(s), entering the call resolution 128 and any ancillary information (such as the dispatched EMS vehicle number, if available, in the case of an ED). This call information is thereafter part of the calling subscriber's profile and may be included in the set of features used to compute the ED risk of the subscriber going forward. It is thus seen that the ED risk prediction of a subscriber may evolve over time due to calls initiated by the subscriber, or (in other examples) due to updated EMR data for the subscriber, or so forth. In some embodiments, it is contemplated to update the ED risk prediction immediately after the call is complete by invoking the ED risk estimation module 94 immediately after completion of the update operation 130, in order to gauge the change in ED risk after handling the current call.

Figure 5:
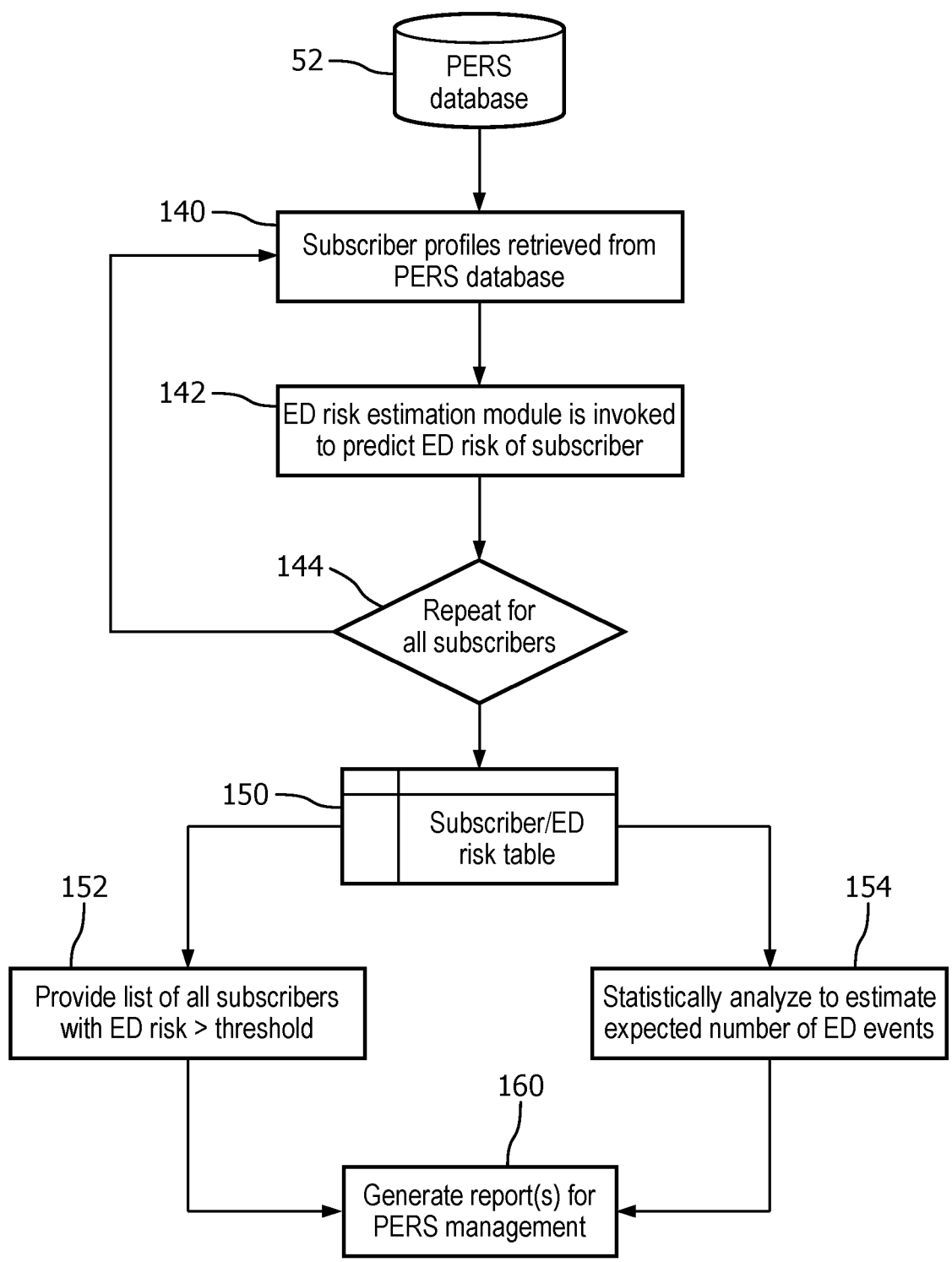
FIG. 5 diagrammatically illustrates a PERS population analysis process suitably performed by the predictive ED assessment module of FIGS. 1 and 2.

With reference to FIG. 5, an illustrative method suitably performed by the ED risk estimation module 94 and statistical module 96 is described. In an operation 140, a (first) subscriber profile is retrieved from the PERS database 52 and values of the set of features is generated from this profile. In an operation 142, the ED risk estimation module 94 is invoked to predict ED risk of the subscriber whose profile was retrieved in operation 140. In a looping operation 144, the operations 140, 142 are repeated for each subscriber in the pool of subscribers served by the PERS service (or for some sub-set of this pool, e.g. if the goal is to provide data for a particular region). If the ED risk model 92 includes components for different risk types, these are each computed for each subscriber in the operations 140, 142, 144. The result of the operations 140, 142, 144 is a table 150 of the ED risk (or risks, if there are different ED risks computed for different risk types) for each subscriber. This table 150 may be variously used. For example, in an operation 152, a list is generated of all subscribers whose ED risk (optionally for a given ED risk type) exceeds some threshold risk. In other words, operation 152 generates a list of the highest-ED risk subscribers. Additionally or alternatively, in an operation 154 the data contained in the table 150 are statistically analyzed, for example to generate an estimate of the expected number of subscribers with one or more ED events over the time horizon (e.g. next 30 days). For example, if the risk for a subscriber to have one or more ED events in the next 30 days is quantified as a probability P, then the expected number of subscribers with one or more ED events may be estimated as $\Sigma_{i \in pop} P_i$ where the summation is over the population (pop) served by the PERS service. The calculation may be done over all PERS subscribers, or over a sub-populations of PERS subscribers defined, for example, by geographical area, medical condition, or membership in a certain health program or health insurance. Another contemplated analysis is to compute the ED risk as a function of time for a patient—a rapidly rising ED risk over time may indicate onset of a serious medical condition. In an operation 160, a suitable report (or reports) is/are generated from the analyses 152, 154 for use by the PERS service management in management operations such as planning staffing levels at the PERS call center 18, providing proactive intervention for subscribers at highest risk for an emergency dispatch (proactive intervention is usually less costly than an emergency ambulance call), for improved coordination with the EMS dispatch center 70, or so forth. Regarding the latter, it is contemplated to access an online mapping service in preparing the report, in order to plot the locations (i.e. residences) of high risk subscribers on a geographical map, in order to aid in planning the deployment of ambulances. Similar report components could also be shared with community health programs directed to prevention of hospital admissions.

Figure 6:
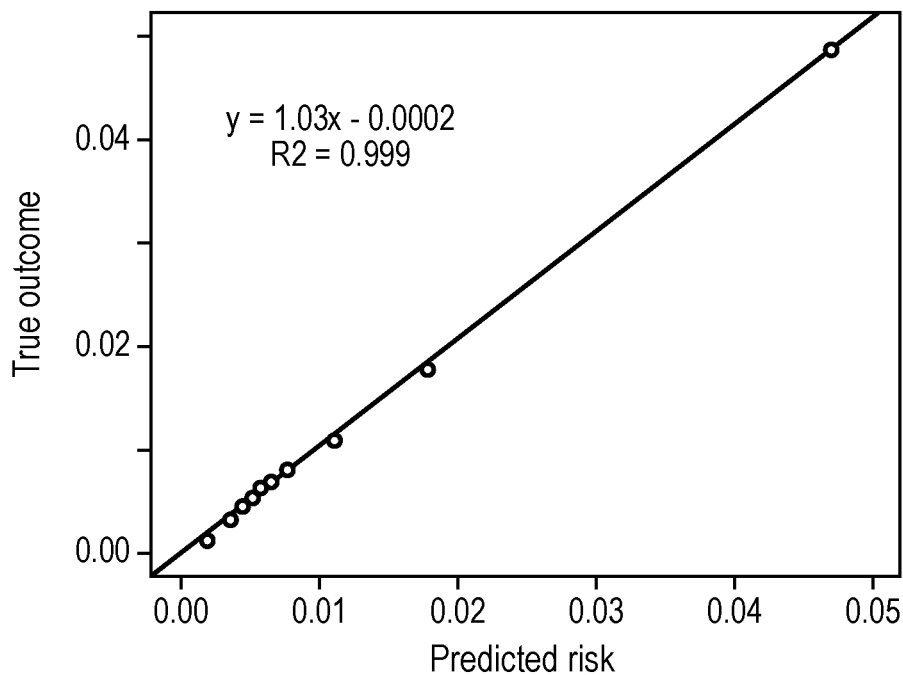
FIG. 6 shows a calibration plot of true outcome vs. predicted ED risk for hospital transport for a future time horizon of 30 days, generated using an illustrative ED risk model described herein.
Figure 7:
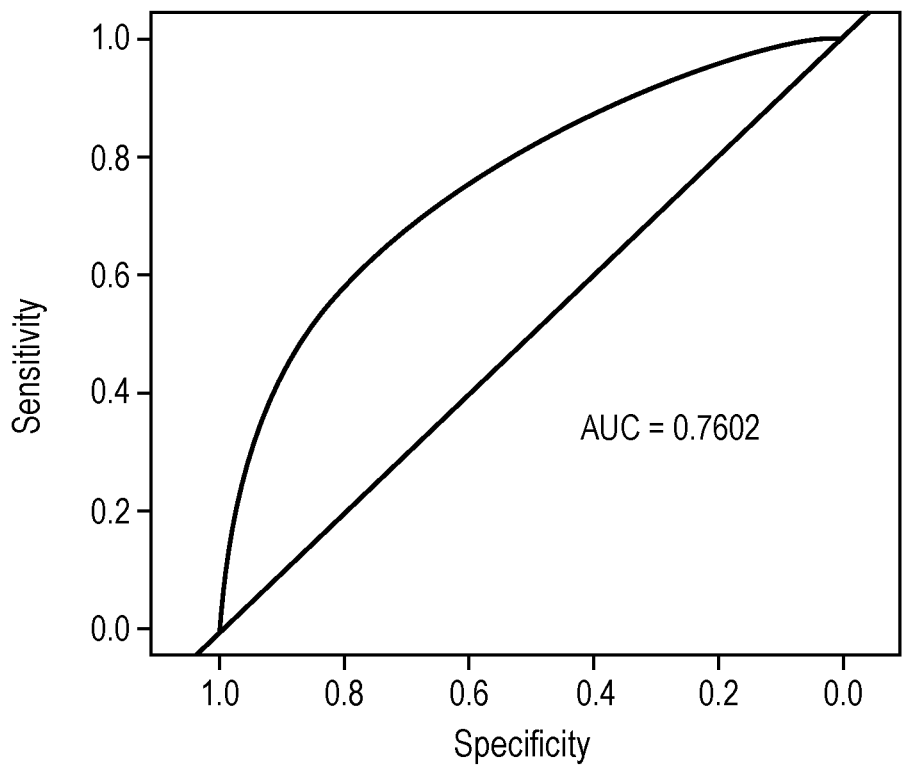
FIG. 7 plots the Receiver Operating Curve (ROC) for a validation cohort, generated during validation of the illustrative ED risk model.
Figure 8:
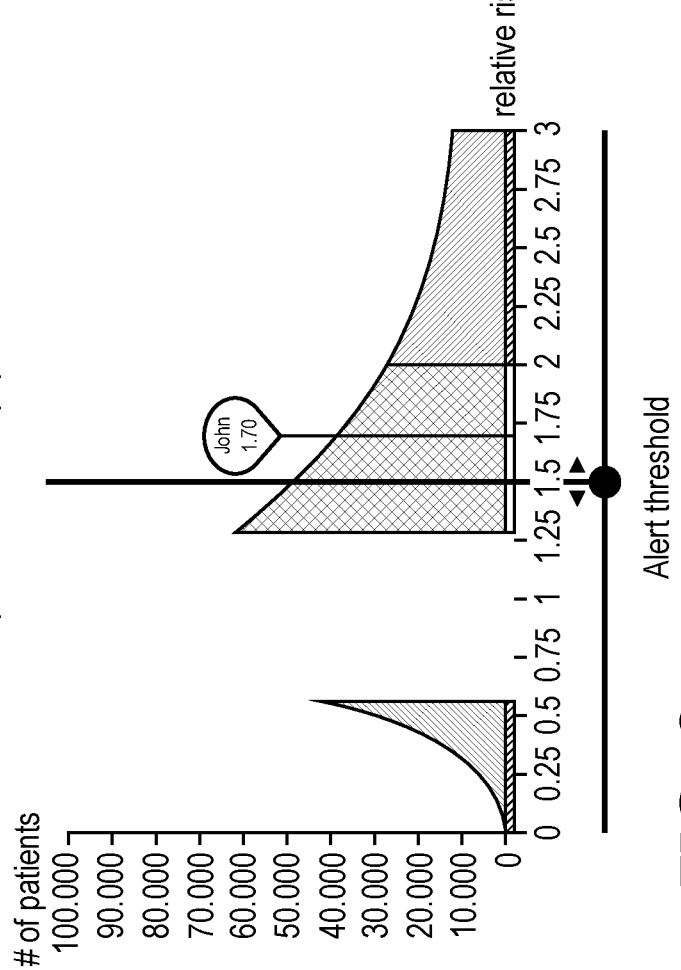
FIG. 8 illustrates a report highlighting subscribers (i.e. "patients") with high ED risk, which may be generated by the ED assessment module of FIGS. 1 and 2.

With reference to FIGS. 6-9, a further illustrative example of the predictive ED risk assessment module 60 is described. The ED risk model training module 90 again employs the multivariate logistic regression model previously described. The illustrative example uses a set of features including, by way of illustration: region features; a feature for each of a plurality of self-reported conditions represented as binary values (e.g. "1" if the subscriber has reported the condition, "0" otherwise); features indicative of the subscriber's support network; and recency and frequency features characterizing calls and ED events of various risk types. FIG. 6 shows a calibration plot of true outcome vs. predicted emergency dispatch (ED) risk for hospital transport for a future time horizon of 30 days. Aggregate means in deciles of risk are shown. Linear regression resulted in y=1.03x− 0.0002 with adjusted $R^2$=0.999. FIG. 7 plots the Receiver Operating Curve (ROC) for the validation cohort, generated by the ED risk model validation operation 110 (see FIG. 3). The area-under-curve (AUC) of the ROC curve is AUC=0.7602. FIG. 8 illustrates a typical report of a type that may be generated by the operation 152 of FIG. 5. In this illustrative example, it is to be understood that the generated report is an interactive online or computer-based report (although it is contemplated to include an option to print a hardcopy version of the report). The left hand window pane of the report of FIG. 8 shows a ranked list, titled "Patient with risk for transport" of those PERS subscribers (referred to as "patients" in the report of FIG. 8) with the highest ED risk. The ED risks are normalized so that an ED risk value of 1.00 corresponds to the average ED risk for the population. The left panel lists those patients whose ED risk is greater than a threshold value of 1.5. As further seen, one subscriber ("John Smith") has been selected (e.g. using an on-screen pointer controlled by a mouse, trackball, trackpad, or other pointing user input device) for further review. The righthand panel illustrates the ED risk for John Smith (ED risk 1.70) highlighted in a histogram plot of ED risks. The histogram is lognormal and peaks at ED risk close to unity, since the ED risk values are normalized so that 1.00 corresponds to the average ED risk for the population. The threshold value of 1.5 for proactive action is also indicated. Thus, the interactive report of FIG. 8 enables PERS management to rapidly identify those subscribers having the highest predicted risk for requiring emergency dispatch in the next thirty days. Based on this information, PERS personnel may take proactive action such as contacting these PERS subscribers, or a caregiver or representative (e.g. a relative, friend, or other contact indicated in the subscriber's PERS profile) to suggest that they schedule a physician's visit soon.

In the illustrative examples, the illustrative predictive risk assessment module 60 predicts the risk of Emergency Dispatch (ED) over a future time horizon, where ED may be variously defined in a particular implementation as the risk of an ambulance call (counted regardless of whether or not the person is actually transported to a hospital) or the more particular risk of actually being transported via ambulance to a hospital (counted only if the person is actually transported to a hospital). It will be appreciated, however, that the disclosed techniques can be readily applied to construct a predictive risk assessment module operating in conjunction with a PERS service to predict other types of risk. For example, the predictive risk assessment module may be designed to predict the risk that the subscriber will be admitted to a nursing home, senior living facility, or other full-time care facility. This information may be useful to trigger proactive action that may enable the subscriber to remain in his or her personal residence.

With reference back to FIG. 1, in some embodiments the subscriber profile and/or the ED risk prediction may be provided to a relative, caregiver, or friend via the mobile device app 82 running on the illustrative mobile device 80, such as a cellular telephone, tablet or slate computer, or the like. This aspect addresses a significant deficiency of some PERS services, namely that they are built upon a subscription relationship which may fail to incorporate third-parties such as relatives, visiting nurses, or friends of the subscriber. Such "informal" caregivers have an interest in knowing about the subscriber's medical condition, and would also benefit from being alerted to a high ED risk.

The disclosed mobile device app 82 can run on multiple mobile devices (only a single device/app instance being shown for illustration in FIG. 1), synchronizing amongst the mobile devices over a cellular telephone network, WiFi network, or other wireless network. A single PERS subscriber can have multiple informal caregivers at the same time (e.g., a spouse, one or more children, a visiting nurse, a neighbor, et cetera), each possessing a cellphone or other mobile device running an instance of the app 82. Communication and synchronization of incident handling, information and responder actions is enhanced by way of data sharing via the mobile device app 82. For instance, when the PERS call center operator notifies a neighbor of a fall and logs this in the PERS system, this is suitably shared amongst all informal caregivers of the subscriber via the app 82 so that all informal caregivers are made aware of the falling incident and are also made aware that it has been dealt with by the neighbor. This enhances team work between informal caregivers.

In the following, some additional contemplated capabilities of the app 82 are described.

In some embodiments, the app 82 allows an informal caregiver to compare the short-term (e.g., 90 days) ED risk of different PERS subscribers. The risk is calculated by the ED risk model 92 using incident data and health data available from the PERS service. This aspect is likely to be of particular value to caregivers such as visiting nurses who care for a number of different PERS subscribers and may wish to compare their relative medical states.

In some embodiments, a longer-term (e.g., one year) calculated ED risk is provided which can be compared to the ED risk of the general population (PERS population or regional or national population).

The app 82 may provide a "risk dashboard" with inputs via which the informal caregiver can enter parameters such as those related to health condition, demographics, hearing and vision condition, or so forth which the PERS subscriber does not currently have. From these entries, the predictive ED risk assessment module 60 calculates the longer-term ED risk if such condition(s) arise, so as to anticipate the longer-term ED risk for the PERS subscriber should he/she develops those conditions.

In another contemplated variant, the app 82 may operate external audible and/or visual alarms, such as operating a Lights over IP interface to cause the room lights to flash in order to notify the caregiver that the PERS service has initiated an ED to the residence of the subscriber.

In the illustrative embodiment, the app 82 operates in conjunction with the illustrative PERS service of FIG. 1 including the predictive ED risk assessment module 60, and accordingly provides information including both subscriber profile information (possibly redacted in accordance with HIPAA or other privacy regulations, and/or in accordance with the subscriber's instructions) and the ED risk prediction for the subscriber. However, it will be appreciated that the app 82 disclosed herein may alternatively be usefully provided in conjunction with a PERS service that does not include the disclosed predictive ED risk assessment module 60—in such embodiments, the app 82 usefully provides informal caregivers with information such as summaries of the latest medically related subscriber calls to the PERS call center and their resolution, but does not provide ED risk prediction.

It will be appreciated that the disclosed approaches implemented by the PERS server computer 50 and/or the call center computer 40 may also be embodied as a non-transitory storage medium storing instructions readable and executable by such a computer 40, 50 to perform the disclosed data processing operations. Such a non-transitory storage medium may, by way of illustration, include: a hard disk drive or other magnetic storage medium; an optical disk or other optical storage medium; a read-only memory (ROM), electronically programmable read-only-memory (PROM), flash memory or other electronic storage medium; various combinations thereof; and so forth. Likewise, the PERS database 52 may be stored on such a storage medium, in some embodiments advantageously embodied as a RAID array or other non-transitory storage medium providing redundancy.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A system comprising a computer programmed to perform operations comprising:
retrieving a first client profile of a first client from a database comprising a plurality of client profiles of a plurality of clients;
generating values from a set of features from the retrieved first client profile, wherein at least one value is representative of an emergency dispatch event, and wherein another value is representative of a check-in call frequency of the first client, wherein the check-in call frequency is determined from calls made by the first client via the system that are classified as being for the purpose of verifying operation of the system;
computing, based on the values for the first client over a future time horizon using an emergency dispatch risk model trained on the plurality of client profiles stored in the database, a likelihood that an ambulance will be dispatched to the first client over the future time horizon, wherein the emergency dispatch model is trained to positively correlate greater check-in call frequency of the first client with greater predicted likelihood that an ambulance will be dispatched to the first client over the future time horizon;
receiving event data generated from one or more new incoming calls from the first client;
computing, using the received event data and likelihood that the ambulance will be dispatched to the first client over the future time horizon, an updated likelihood that the ambulance will be dispatched to the first client over the future time horizon;
ranking the updated likelihood that the ambulance will be dispatched to the first client over the future time horizon against likelihoods that ambulances will be dispatched to others of the plurality of clients over the future time horizon;
prioritizing, based on the ranking, an automated allocation of emergency resources to the one or more clients, including the first client; and
automatically allocating the emergency resources in accordance with the prioritizing.

2. The system of claim 1, wherein the computer is further programmed to perform the operations comprising:
retrieving a second client profile of a second client from the database;
generating values from a second set of features from the retrieved second client profile, wherein at least one value from the second set is representative of an emergency dispatch event, and wherein another value of the second set is representative of a check-in call frequency of the second client, wherein the check-in call frequency is determined from calls made by the second client via the system that are classified as being for the purpose of verifying operation of the system;
computing, based on the values for the second client over a future time horizon using the emergency dispatch risk model, a likelihood that an ambulance will be dispatched to the second client over the future time horizon;
receiving event data generated from one or more new incoming calls from the second client;
computing, using the received event data and likelihood that the ambulance will be dispatched to the second client over the future time horizon, an updated likelihood that the ambulance will be dispatched to the second client over the future time horizon; and
ranking the updated likelihood that the ambulance will be dispatched to the second client over the future time horizon against likelihoods that ambulances will be dispatched to others of the plurality of clients over the future time horizon.

3. The system of claim 1, wherein the set of features further includes at least one of: an emergency dispatch event frequency feature; a plurality of different emergency dispatch event recency features, each different emergency dispatch event recency feature indicating recency of an emergency dispatch for a different type of medical event; and an accidental call frequency feature, wherein the emergency dispatch risk model positively correlates higher accidental call frequency with greater predicted likelihood that an ambulance will be dispatched to the first client over the future time horizon.

4. The system of claim 1, wherein the plurality of client profiles stored in the database comprises a national population.

5. The system of claim 1 wherein the plurality of client profiles stored in the database comprises a regional population.

6. The system of claim 1, wherein the future time horizon is a short-term time horizon.

7. The system of claim 1, wherein the future time horizon is a long-term time horizon.

8. The system of claim 1, wherein the set of features includes at least one emergency dispatch event frequency feature.

9. The system of claim 1, wherein the set of features includes a plurality of different emergency dispatch event recency features, each different emergency dispatch event recency feature indicating recency of an emergency dispatch for a different type of medical event.

10. The system of claim 1, wherein the set of features includes an accidental call frequency feature and the emergency dispatch risk model positively correlates higher accidental call number or frequency with higher predicted emergency dispatch risk.

11. A method comprising:
retrieving, at a computing device, a first client profile of a first client from a database comprising a plurality of client profiles of a plurality of clients;
generating, using a processor of the computing device, values from a set of features from the retrieved first client profile, wherein at least one value is representative of an emergency dispatch event, and wherein another value is representative of a check-in call frequency of the first client, wherein the check-in call frequency is determined from calls made by the first client via the system that are classified as being for the purpose of verifying operation of the system;
computing, using the processor, based on the values for the first client over a future time horizon using an emergency dispatch risk model trained on the plurality of client profiles stored in the database, a likelihood that an ambulance will be dispatched to the first client over the future time horizon, wherein the emergency dispatch model is trained to positively correlate greater check-in call frequency of the first client with greater predicted likelihood that an ambulance will be dispatched to the first client over the future time horizon;
receiving, at the computing device, event data generated from one or more new incoming calls from the first client profile;
computing, using the processor and using the received event data and likelihood that the ambulance will be dispatched to the first client over the future time horizon, an updated likelihood that the ambulance will be dispatched to the first client over the future time horizon;

ranking, using the processor, the updated likelihood that the ambulance will be dispatched to the first client over the future time horizon against likelihoods that ambulances will be dispatched to others of the plurality of clients over the future time horizon;

prioritizing, using the processor based on the ranking, an automated allocation of emergency resources to the one or more clients, including the first client; and automatically allocating, using the processor, the emergency resources in accordance with the prioritizing.

12. The method of claim 11, wherein the computer is further programmed to perform the operations comprising:

retrieving, at the computing device, a second client profile of a second client from the database;

generating, using the processor, values from a second set of features from the retrieved second client profile, wherein at least one value from the second set is representative of an emergency dispatch event, and wherein another value from the second set is representative of a check-in call frequency of the second client, wherein the check-in call frequency is determined from calls made by the second client via the system that are classified as being for the purpose of verifying operation of the system;

computing, using the processor, based on the values over a future time horizon using the emergency dispatch risk model, a likelihood that an ambulance will be dispatched to the second client over the future time horizon;

receiving, at the computing device, event data generated from one or more new incoming calls from the second client;

computing, using the processor and using the received event data and likelihood that the ambulance will be dispatched to the second client over the future time horizon, an updated likelihood that the ambulance will be dispatched to the second client over the future time horizon; and ranking, using the processor, the updated likelihood that the ambulance will be dispatched to the second client over the future time horizon against likelihoods that ambulances will be dispatched to others of the plurality of clients over the future time horizon.

13. The method of claim 11, wherein the plurality of client profiles stored in the database comprises a national population.

14. The method of claim 11, wherein the plurality of client profiles stored in the database comprises a regional population.

15. The method of claim 11, wherein the future time horizon is selected from at least one of: a short-term time horizon and a long-term time horizon.

* * * * *